United States Patent
Bancroft

[19]
[11] Patent Number: 5,447,168
[45] Date of Patent: Sep. 5, 1995

[54] MOUTHGUARD

[76] Inventor: James J. Bancroft, 43 Mercer Ave., Englewood Cliffs, N.J. 07632

[21] Appl. No.: 316,866
[22] Filed: Oct. 3, 1994
[51] Int. Cl.$^6$ ............................................. A61C 5/14
[52] U.S. Cl. .................................... 128/859; 128/861
[58] Field of Search .................... 128/848, 859–862; 2/2

[56] References Cited

U.S. PATENT DOCUMENTS

| | | | |
|---|---|---|---|
| 1,775,718 | 9/1930 | Garvey | 128/848 |
| 2,142,614 | 1/1939 | Mitchell | 128/859 |
| 2,424,533 | 7/1947 | Faires | 128/861 |
| 2,483,157 | 9/1949 | Singer | 128/861 |
| 2,574,623 | 11/1951 | Clyde | 128/848 |
| 2,600,025 | 6/1952 | Sage | 128/860 |
| 2,627,268 | 2/1953 | Leppich | 128/861 |
| 3,187,746 | 6/1965 | Gerber | 128/859 |
| 4,031,888 | 6/1977 | Walters | 128/859 |

*Primary Examiner*—Michael A. Brown
*Attorney, Agent, or Firm*—Howrey & Simon; Richard S. Meyer; Leo J. Jennings

[57] ABSTRACT

A mouthguard for protecting lips against impact trauma on orthodontic appliances (braces), protecting teeth from sports trauma, protecting teeth from clashing together or grinding; and, protecting the temporomandibular joint (T.M.J.) from traumas due to a blow to the mandible. The mouthpiece comprises a curved flexible element, having two or more substantially central apertures extending therethrough and a notched portion on the upper and lower surface thereof. On the inner posterior surface of the element, an inwardly projecting portion extends at right angles thereto on each side of the aperture and designed to be grasped by the teeth. The mouthguard lays against the outer surface of the teeth with the curved flexible element and extends into the buccal folds superiorly and interiorly of the cheek where the muscles hold it in place. A groove is positioned lengthwise along the posterior curved element above and below the right angle of the projecting portion for purposes of flexibility and to allow the muscles of the cheek to press the element close to the bone for better retention and comfort. The teeth engage both sides of the inwardly projecting element which prevent the teeth from clashing together and protects the temporomandibular joint (T.M.J.). The anterior central apertures permit easy breathing. The mouthguard is retained by the muscles of the lips and cheeks, causes no gag reflex and is simple, comfortable and protective.

15 Claims, 1 Drawing Sheet

MOUTHGUARD

BACKGROUND OF THE INVENTION

This invention relates to mouthguards and in particularly to a new and improved mouthguard which is retained in position by the muscles of the lips and cheeks and produces no gag reflex. It is designed to fit comfortably over orthodontic appliances or to fit over the teeth naturally without orthodontic appliances of both maxillary and mandibular arches.

The prior art includes U.S. Pat. No. 2,590,118 to Oddo which discloses a mouthpiece having upper and lower channels for the teeth and pivotal front portions of the guard to permit opening of the mouth.

U.S. Pat. No. 4,114,614 to Kesling, discloses a mouthguard appliance comprising a pair of allochiral arch shaped members hingedly connected together and made of a resilient material. The hinge permits folding of the arch shaped members together to retain the members in place on the arches. The teeth contact a plurality of ridges to hold the mouthguard in position.

The present patent discloses a device which is simple and comfortable and does not join across the rear of the mouth and includes an anterior aperture to facilitate breathing. The prior art patents do not disclose a similar structure.

SUMMARY OF THE INVENTION

This invention relates to a new and improved mouthpiece, comprising a curved elongated frame member, having one or more anterior apertures in the central portion thereof and a central notch on the upper surface thereof. The mouthpiece frame further includes a first and a second outwardly projecting portion on the rear surface thereof, which can be grasped on both sides by the teeth to hold the mouthpiece in position. The mouthpiece as described protects one's teeth while eliminating the tendency to gag, which is a problem with most mouthguards. It also protects lips from impacting on the teeth or orthodontic appliances in the event of facial trauma. It further protects the temporomandibular joint (T.M.J.).

Accordingly, an object of this invention is to provide a new and improved flexible mouthguard.

Another object of this invention is to provide a new and improved flexible mouthguard which comprises a frame member which is held in position by the reflexes of the cheeks and lips against the teeth and includes outwardly projecting members which can be grasped on both sides by the teeth.

Another object of this invention is to provide flexible extensions of these buccal flanges via a stress relief groove (joint) so that these extensions can respond easily to the pressure of the muscles and lay comfortably in the buccal folds.

A further object of this invention is to provide a new and improved flexible mouthguard which is simple to use, inexpensive and readily used by the wearer since it is merely inserted into one's mouth and retained by the muscles and outwardly projecting portions which can be grasped by one's teeth without problems caused by the gaging reflex.

DESCRIPTION OF THE DRAWINGS The above and other objects and advantages of this invention may be more clearly seen when viewed in conjunction with the accompanying drawings wherein:

FIG. 1 is a front perspective view of the invention;
FIG. 2 is a rear view of the invention with a curved frame element stretched out into a vertical plane; and
FIG. 3 is a top view of the invention.

DETAILED DESCRIPTION OF THE INVENTION

Figure 1:
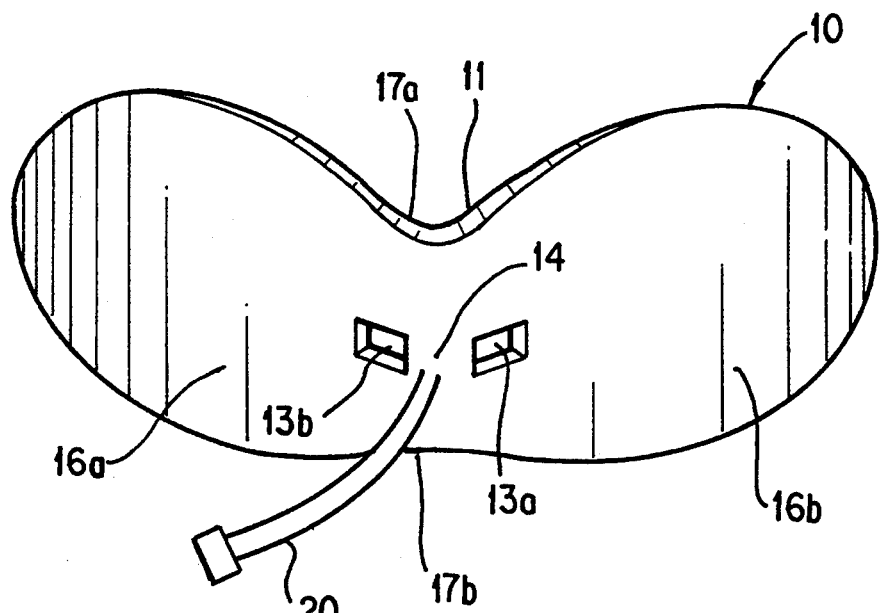
Figure 2:
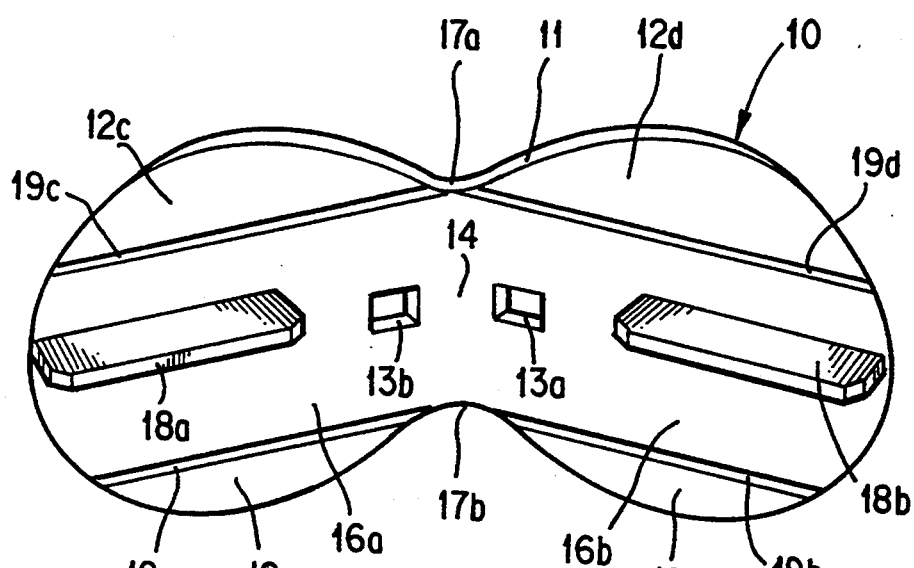
Figure 3:
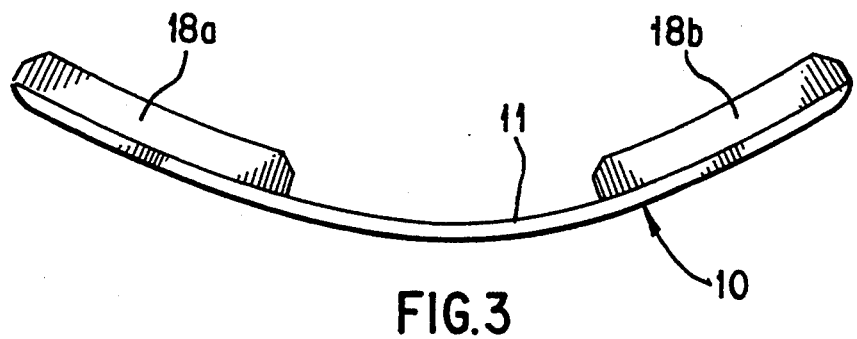

Referring now to the drawings, the invention comprises a mouthguard 10 having a curved frame member 11 which fits against the inside of the lips, cheeks and outside of teeth. The curvature is designed to accommodate the contour of the user's mouth. The mouthpiece includes two or more apertures 13a and 13b which facilitate breathing with the mouthpiece in place. In the drawings, a pair of rectangular apertures are shown with a portion 14 of the frame 11 separating the apertures. This arrangement provides additional strength although it is feasible to have a single aperture or a plurality of apertures to provide an opening for breathing. The frame member 11 basically includes two enlarged curved end members 15a and 16b which join at a central recessed slot 17a and 17b which is designed to provide additional comfort in using the mouthguard 10.

The rear portion of the mouthguard includes an inward extension 18a and 18b on each side of the apertures 13a and 13b. The extensions protrude inwardly at a right angle to from the rear of frame 11. The mouthguard 10 lays against the outer surface of the teeth which grasp both sides of the inwardly projecting elements 18a and 18b. This provides protection to the temporomandibular joint (TMJ) and posterior teeth against straight-on blows. The curved end members 16a and 16b have horizontally running flexible grooves (joints), which function as hinges 19a–d, which allow the muscles in the cheek to press the extensions 12a, 12b,12c, 12d close to the bone for better retention and comfort. With the teeth engaged from both sides of the inwardly projecting elements the teeth are prevented from clashing together and the wearer is protected from TMJ. The mouthguard is retained by the muscles of the lips and cheek and causes no gag reflex and is simple, comfortable and protective.

The lengthwise horizontal grooves 19a, 19b, 19c, 19d on each side of the posterior extension provide flexibility particularly during insertion of the mouthguard 10. The flexible mouthguard is also normally in a curved position to permit ease of installation in the user's mouth. If desired, a helmet strap attachment 20 can be molded to the central portion 14 of the outer frame element, as shown schematically in FIG. 1.

The mouthguard protects the lips against impact trauma particularly on orthodontic appliances. The use of mouthguards with orthodontic appliances or braces is extremely difficult with the present designs. The mouthguard 10 also protects the teeth from trauma and clashing together or grinding and protects the TMJ from traumas due to a blow to the mandible.

While the invention has been explained by a detailed description of certain specific embodiments, it is understood that various modifications and substitutions can be made in any of them within the scope of the appended claims which are intended also to include equivalents of such embodiments.

What is claimed is:

1. A mouthguard for insertion into a wearer's mouth to protect fine wearer's teeth and terndoromandibular joint from trauma, said mouthguard comprising:

a generally curved, flexible member including a central portion for protecting the wearer's anterior teeth and two, end members each extending rearwardly from said central portion for protecting the wearer's posterior teeth, said flexible member having a front surface adjacent the wearer's lips and cheeks, a rear surface adjacent the wearer's anterior and posterior teeth when the mouthguard is inserted into the wearer's mouth, and a thickness defined by the distance between the front and rear surfaces;

a first groove extending into one of said front and rear surfaces a predetermined depth less than the thickness of said flexible member, said groove defining a first hinge permitting flexing of a portion of the flexible member about said hinge to conform to the wearer's mouth; and a pair of opposed, bite tabs projecting inwardly from said end members and adapted to be engaged by the wearer's posterior teeth.

2. A mouthguard in accordance with claim 1, wherein said first groove extends generally horizontally across the rear surface of the mouthguard when placed in the wearer's mouth, and said portion of the flexible member being flexible about said first hinge comprises a first outward extension of the flexible member disposed above said first hinge.

3. A mouthguard in accordance with claim 2, further comprising a second groove extending generally horizontally across and into another portion of said rear surface a predetermined depth less than the thickness of said flexible member, said second groove defining a second hinge permitting flexing of a second outward extension of said flexible member disposed below said second hinge.

4. A mouthguard in accordance with claim 3, wherein said bite tabs are located between said first groove and said second groove.

5. A mouthguard in accordance with claim 4, wherein said first groove extends across the entire longitudinal extent of said central portion and end members in a position segregating said first outward extension into two distinct upper extensions having an outer perimeter conforming to the upper portion of a wearer's mouth.

6. A mouthguard in accordance with claim 5, wherein said second groove extends across the entire longitudinal extent of said central portion and end member's in a position segregating said second outward extension into two distinct lower extensions having an outer perimeter conforming to the lower portion of the wearer's mouth.

7. A mouthguard in accordance with claim 6, wherein said mouthguard is generally symmetrical about longitudinal and vertical axes and the distance between the outer perimeter of the upper extensions and the outer perimeter of the lower extensions is at a minimum at the center of the mouthguard.

8. A mouthguard in accordance with claim 1, further comprising at least one aperture in said flexible member providing an opening to facilitate breathing.

9. A mouthguard in accordance with claim 8, wherein said at least one aperture is provided in said central portion of said flexible member.

10. A mouthguard in accordance with claim 9, wherein said at least one aperture comprises two symmetrically disposed apertures.

11. A mouthguard in accordance with claim 1, wherein the wearer's teeth include orthodontic braces and said first hinge permits flexing to conform to the wearer's mouth and protect the lips against impacting the braces.

12. A mouthguard in accordance with claim 1, further comprising a helmet strap attachment connected to said front surface of said flexible member.

13. A mouthguard for insertion into a wearer's mouth to protect the wearer's teeth and temporomandibular joint from trauma, comprising:

a curved flexible member adaptable into a substantially u-shaped profile having a front surface and a rear surface, wherein said member has a first side portion, a second side portion, and a central portion, said first and second side portions separated in a lateral direction from each other by said central portion;

an aperture extending through said central portion;

a first bite tab projecting inwardly from said rear surface of said first side portion;

a first groove extending along said rear surface of said first side portion, to facilitate flexing of said member along said first groove to conform to the wearer's mouth;

a second bite tab projecting inwardly from said rear surface of said second side portion; and a second groove extending along said rear surface of said second side portion, to facilitate flexing of said member along said first groove to conform to the wearer's mouth.

14. A mouthguard in accordance with claim 13, wherein said first side portion further comprises a third groove extending across said rear surface of said first side portion and said second side portion further comprises a fourth groove extending across said rear surface of said second side portion.

15. A mouthguard in accordance with claim 14, wherein said first bite tab is located between said first groove and said third groove, and said second bite tab is located between said second groove and said fourth groove.

* * * * *

UNITED STATES PATENT AND TRADEMARK OFFICE
CERTIFICATE OF CORRECTION

PATENT NO. : 5,447,168
APPLICATION NO. : 08/316866
DATED : September 5, 1995
INVENTOR(S) : James J. Bancroft It is certified that error appears in the above-identified patent and that said Letters Patent is hereby corrected as shown below:

At col. 1, ine 6: Please delete "and in", and insert --and--.
At col. 1, line 68. Please delete "gaging", and insert --gagging--.
At col. 3, line 3: Please delete "fine", and insert --the--.
At col. 3, line 3: Please delete "terndoromandibular", and insert --temporomandibular--.
At col. 3, line 7. Please delete "two,", and insert --two--.
At col. 3, lines 54-55. Please delete "member's", and insert --members--.

Signed and Sealed this

Twenty-first Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 5,447,168  
APPLICATION NO. : 08/316866  
DATED : September 5, 1995  
INVENTOR(S) : James J. Bancroft It is certified that error appears in the above-identified patent and that said Letters Patent is hereby corrected as shown below:

At col. 1, line 6: Please delete "and in", and insert --and--.
At col. 1, line 68. Please delete "gaging", and insert --gagging--.
At col. 2, line 26. Please delete "15a", and insert --16a--.
At col. 3, line 3: Please delete "fine", and insert --the--
At col. 3, line 3: Please delete "terndoromandibular", and insert --temporomandibular--.
At col. 3, line 7. Please delete "two,", and insert --two--.
At col. 3, lines 54-55. Please delete "member's", and insert --members--.

Signed and Sealed this

Fifth Day of December, 2006

JON W. DUDAS  
*Director of the United States Patent and Trademark Office*